(12) United States Patent
Kuo

(10) Patent No.: US 6,599,048 B2
(45) Date of Patent: Jul. 29, 2003

(54) TOOTHBRUSH FOR MASSAGING AND PROTECTING GUMS

(76) Inventor: Youti Kuo, 88 Foxbourne Rd., Penfield, NY (US) 14526

( * ) Notice: Subject to any disclaimer, the term of this patent is extended or adjusted under 35 U.S.C. 154(b) by 0 days.

(21) Appl. No.: 09/981,604

(22) Filed: Oct. 18, 2001

(65) Prior Publication Data

US 2003/0077107 A1 Apr. 24, 2003

(51) Int. Cl.⁷ ............................................. A46B 11/04
(52) U.S. Cl. ................. 401/269; 401/188 R; 401/184; 401/286; 15/110
(58) Field of Search ............................... 401/184, 282, 401/286, 187, 188 R, 188 A, 269; 15/110, 106, 167.1

(56) References Cited

U.S. PATENT DOCUMENTS

| | | | |
|---|---|---|---|
| 1,251,250 A | 12/1917 | Libby | |
| 2,088,839 A | 8/1937 | Coney et al. ................. | 15/188 |
| 2,117,174 A | * 5/1938 | Jones ........................... | 15/110 |
| 3,258,805 A | 7/1966 | Rossnan ....................... | 15/110 |
| 3,398,421 A | * 8/1968 | Rasnbaum .................... | 15/110 |
| 3,553,759 A | 1/1971 | Kramer et al. ................. | 15/110 |
| 4,277,862 A | 7/1981 | Weideman .................... | 15/110 |
| 5,033,154 A | 7/1991 | Marchand et al. .......... | 15/167.1 |
| 5,346,324 A | 9/1994 | Kuo ........................... | 401/146 |
| 5,628,082 A | 5/1997 | Moskovich ................... | 15/110 |
| 6,254,390 B1 | 7/2001 | Wagner ....................... | 433/216 |

* cited by examiner

Primary Examiner—David J. Walczak

(57) ABSTRACT

A toothbrush that utilizes a replaceable brush head having rubber gum guard on its top surface and a triangular shaped rubber pad on its bottom surface. The rubber gum guard is shorter than the height of the bristles and is positioned on the peripheral edge of a brush head for functioning as a sensor for providing feedback to prevent brushing at excessive pressures and improper angles as well as for massaging the gumlines without the risk of gum damages. The triangular shaped rubber pad is for conforming to and massaging gumlines at the back of teeth. The replaceable brush head having the rubber gum guard and massaging pad features is economically used in conjunction with a permanent handle that dispenses dentifrice material to the top of bristles. The handle has a resilient contractible connector for secure mounting of the replaceable brush head.

8 Claims, 13 Drawing Sheets

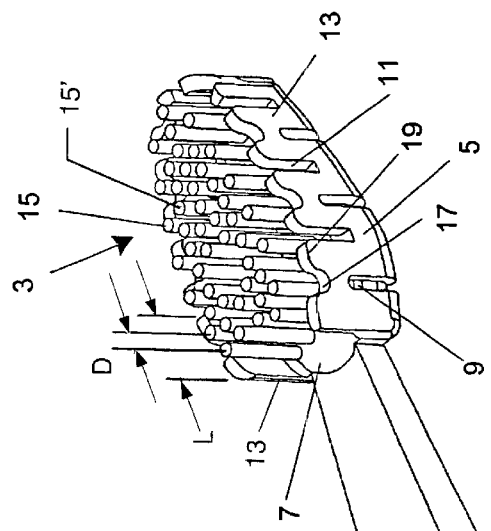
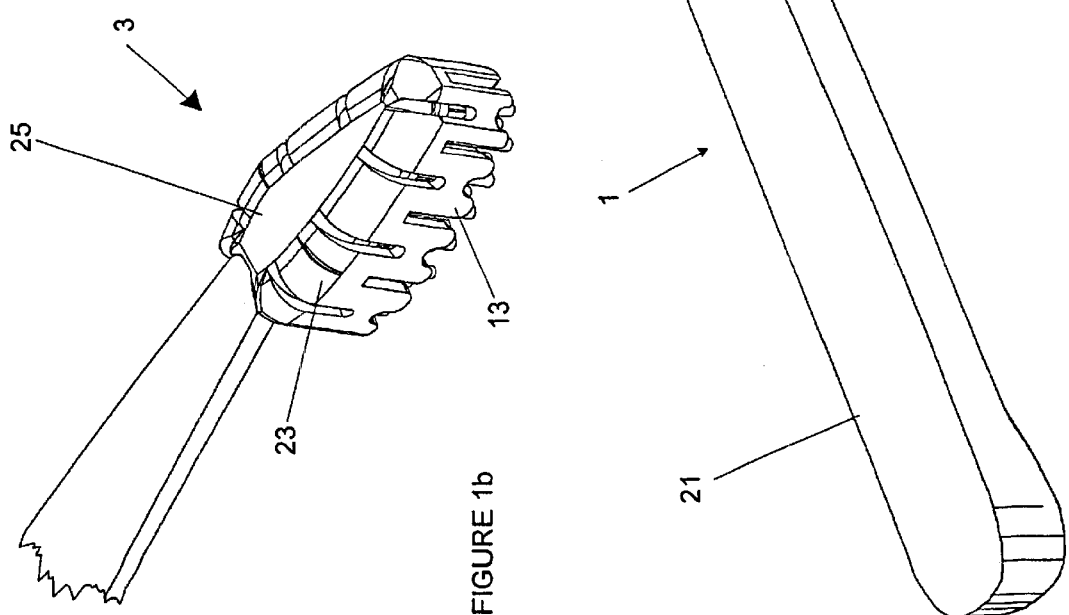
FIGURE 1a
FIGURE 1b

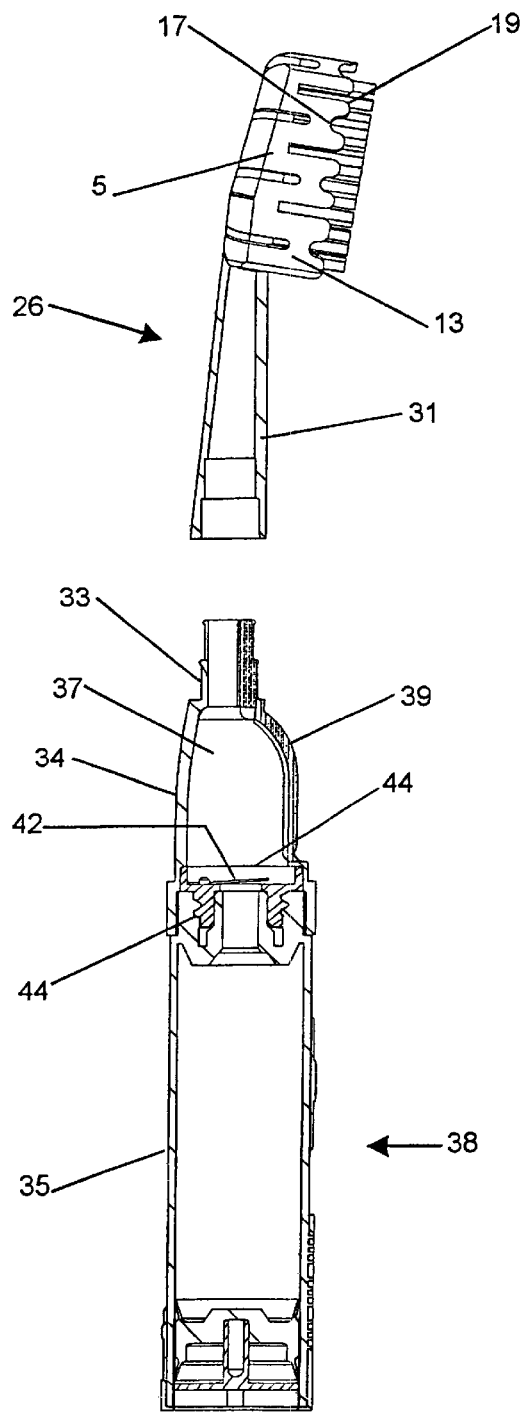
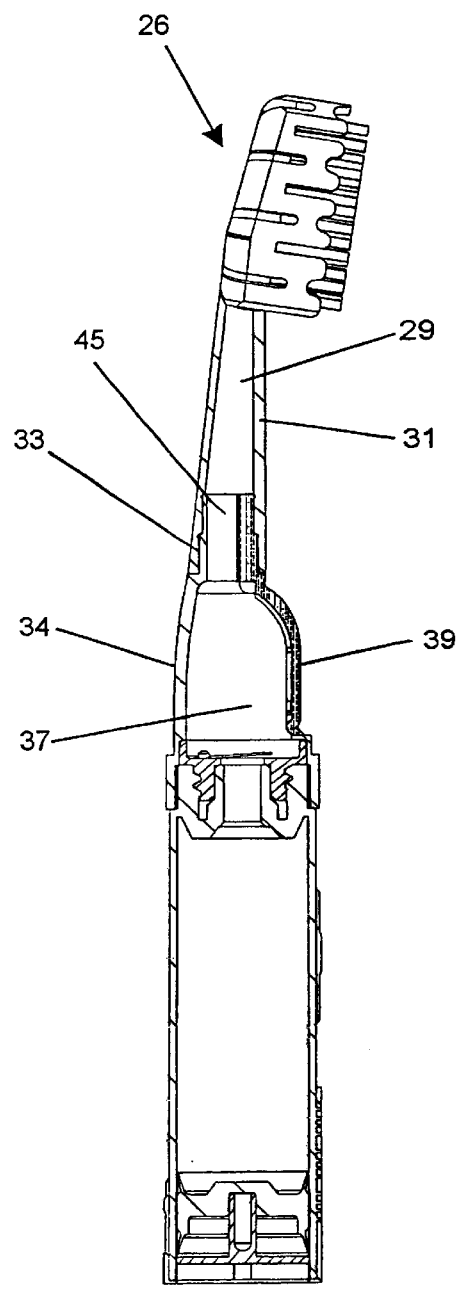
FIGURE 3b
FIGURE 3c

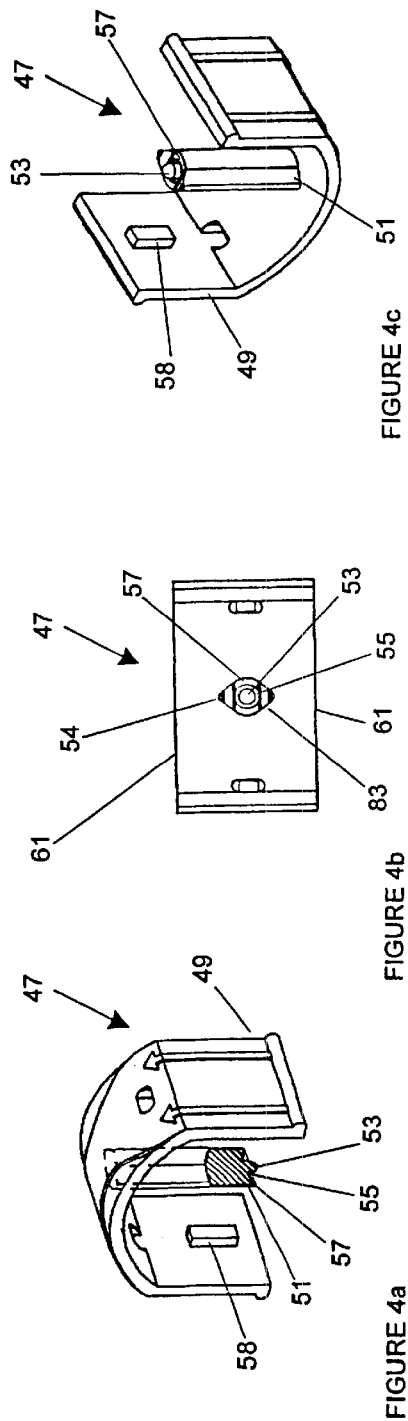
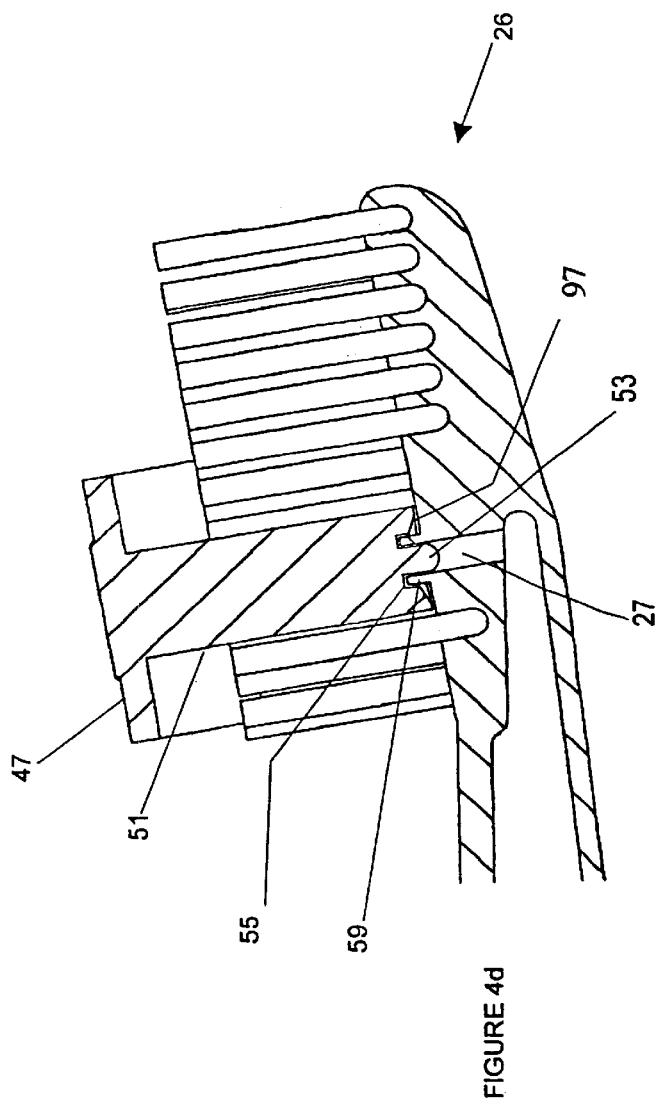
FIGURE 4c
FIGURE 4b
FIGURE 4a
FIGURE 4d

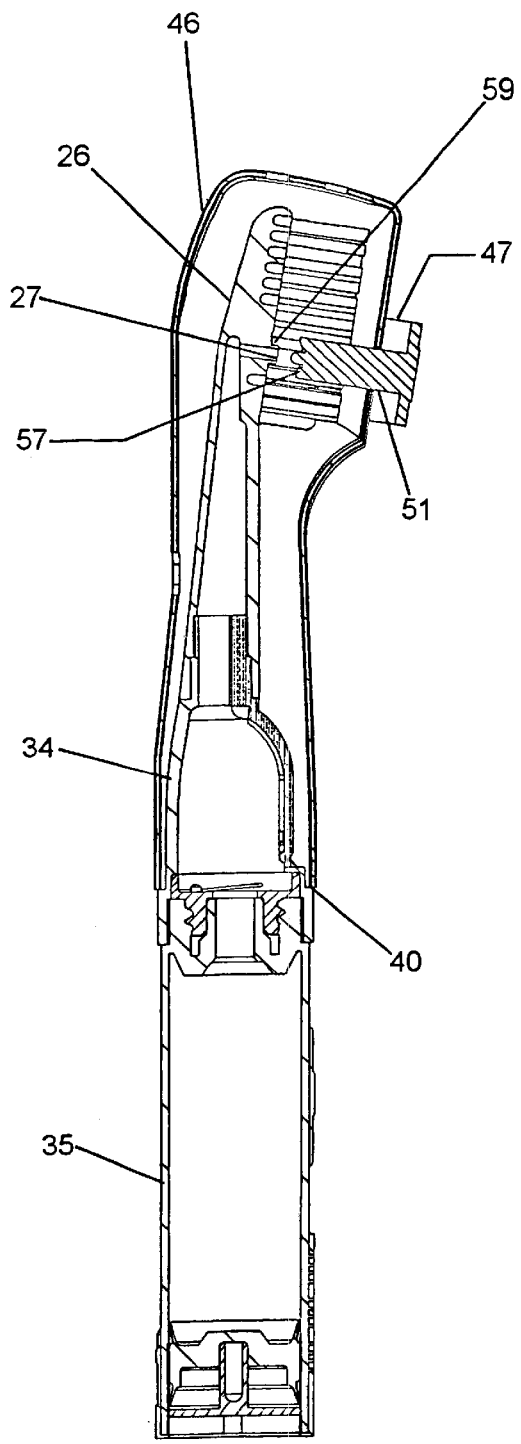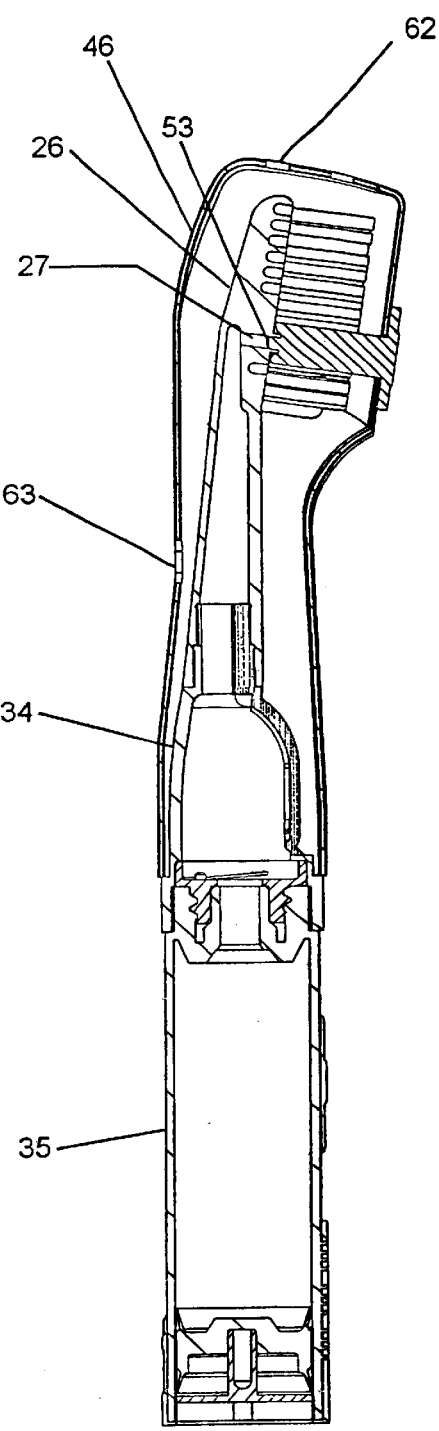
FIGURE 5a
FIGURE 5b

TOOTHBRUSH FOR MASSAGING AND PROTECTING GUMS

BACKGROUND OF THE INVENTION

It has long been recognized that toothbrush abrasion and gum bleeding can be caused by brushing at excessive pressure and at improper angle and that bacteria build up caused by prolonged use of a brush head. Notwithstanding the development of various types of toothbrushes to provide improved dental care, these problems still persist. Therefore, it is desirable to have a toothbrush that prevents brushing at excessive pressures and at improper angles and provides for gum care. It is also desirable to massage gumlines in general and problem areas in particular, by using resilient rubber material for stimulation and strengthening of gum tissues without causing injuring to the gumlines by bristles. To avoid bacteria accumulation, it is desirable to have the massaging features built in a replaceable brush head which then can be replaced frequently and economically in conjunction with the use of a handle that stores and pumps dentifrice material from inside the handle to bristle surface. For the reliable use of a replaceable brush head, it is desirable for the handle to have a contractible connector having a resilient rubber segment for securely mounting it to the replaceable brush head, and to have a sealing rod with air-tight features for sealing the spout opening for preventing drying of dentifrice material. For gum care for elimination of bacteria contamination and for convenience and low cost, it is desirable to include all the above functions in one toothbrush.

(1) Field of the Invention

The present invention relates to a toothbrush with features that provide enhanced care for teeth and gums. In particular, the invention provides means for protecting against brushing at improper pressures and angles and for massaging gumlines. The invention encompasses toothbrushes with fixed as well as removable brush heads.

(2) Description of the Prior Art

On brushing pressure, U.S. Pat. No. 5,315,732 by Huefner, et al. describes a toothbrush having adjustable brushing pressure by using a movable bristle head with respect to a handle. The toothbrush contains adjustable springs to permit presetting brush pressure to make a user aware of exceeding the preset pressure. This allows the user to learn to brush at a pressure that permits good cleaning without damaging gingival tissues. The configuration of the spring loading is complex and is subject to becoming disassembled while in use. U.S. Pat. No. 5,323,504 by McCusker used a deformable, non-resilient intermediate segment between a bristle head and a handle for changing the angular relationship between the bristle head and the handle. A user is made aware of excessive brushing pressure if the angular relationship is changed after brushing. This approach is a hindsight in nature since as any adjustment is done after improper brushing angles have been used.

Other flexible brush head approaches are exemplified by U.S. Pat. No. 5,054,154 by Schiffer, et al. and U.S. Pat. No. 5,765,254 by O'Halloran. The former uses an elastic segment between a handle and a brush head to alleviate excessive brushing pressure. The elastic segment is formed by filling slots with elastic polymeric/copolymetric plastic material. The latter used a semi-rigid material to support the bristles. Although brush heads of these methods are flexible, they do not pre-warn the user of exceeding a safe brushing pressure.

The limit of brushing pressure is also addressed by some patents on electrical toothbrushes. U.S. Pat. No. 5,784,742 by Giuliani, et al. uses an adaptive load sensor to monitor the current drawn by its drive assembly to determine the mechanical load during brushing. If the sensed load voltage exceeds an adaptive threshold signal that represents the pressure limit, the load sensor assembly de-energizes the drive assembly and generates an alarm signal. U.S. Pat. No. 5,815,872 by Meginniss, III, et al. employs a rigid brush head shield which contains an electrical switch contact and is positioned close to a brush head which has a hinge-like flexible neck. When the brushing pressure is too high, it causes the brush head to touch the brush head shield so as to close the switch contact, which results in visual indication of exceeding the maximum pressure. A similar approach is described in U.S. Pat. No. 5,331,707 by Irizarry. The patentee uses a spring-loaded housing wall to activate an electrical audible alarm when the housing wall is contacted by the deflection of a toothbrush shaft. Unlike the above patents which require the use of an electrical power source, no electrical power is used in the invention described in U.S. Pat. No. 5,355,544 by Dirksing. Here, the patentee uses a magnetic latching and unlatching mechanism to indicate whether the maximum brushing pressure is exceeded. However, the magnetic attachments could break loose during brushing and cause gum injury.

On brushing angle, U.S. Pat. No. 5,033,154 by Marchard, et al. reveals a toothbrush a structure using a removable brush head which may be attached to a handle at different angles to provide selections for a user. This adjustable feature, however, does not ensure brushing at proper angles all the time since a user is provided no feedback during brushing. In view of the 45 degree brushing angle recommended by dentists, the angled bristle pattern of U.S. Pat. No. 4,852,202 by Ledwitz employs a toothbrush having an angled bristle pattern which is intended to eliminate canting of the toothbrush during brushing. The patent assumes that the user will maintain a constant brushing angle. However, the angled bristles still can cause gum damages by those users who employ inconsistent brushing angles.

On gum stimulation and protection, U.S. Pat. No. 5,342,284 by Lemon, et al. describes a soft brush having a high density of thin long fibers surrounded by short fibers. The soft brush uses the long fibers for penetrating the interstitial spaces between teeth for gum stimulation without causing tissue damage. Its disadvantage is that the soft bristles can be easily over bent so as to reduce its effectiveness for cleaning. U.S. Pat. No. 5,729,859 by Guffin, III deals with gum protection for an infant by having a guard attached to a toothbrush. The guard remains outside a child's mouth during brushing so that it cannot be swallowed. While the toothbrush is designed for safety, it does not protect gums from brushing at excessive pressures and improper angles. Another patent on gum protection is U.S. Pat. No. 5,860,183 by Kam. It discloses a toothbrush having a rubber bumper attached to the front end face of a brush head by means of a water soluble spacer or an adhesive. Besides gum protection, the rubber bumper also serves as a wear indicator as it dissolves after a predetermined number of wetting cycles. Brushing with a dissolvable or detachable bumper material inside the mouth creates a substantiated safety risk.

Furthermore, several prior art patents provide toothbrushes that incorporate rubber bristles in a brush head. U.S. Pat. No. 1,251,250 by Libby describes a brush head having a sleeve of resilient rubber bristles attached to its bristle platform which has hair bristles in the central portion. The multiple rows of rubber bristles are equally aligned on both sides of the central hair bristles and the ends of the rubber bristles are approximately level with the ends of the hair bristles. These rubber bristles are for massaging gums. Being at the same height, both the rubber and the hair bristles are depressed indiscriminately during brushing, therefore, the bristle configuration does provide distinct feel to the user for alerting the excessive brushing pressures or improper brushing angles.

U.S. Pat. No. 2,088,839 by Coney et al. describes a method of securing rubber bristles in a strip which is mounting on a groove positioned at a distance from an edge of a bristle platform of a brush head. Two strips are positioned on each side of the bristle platform which includes a central bristle section. Only for massaging purpose, the stiffness of the rubber bristles in the longitudinal and the transverse directions of the rubber bristle strip are of the same order of magnitude. During brushing in the direction of the bristle strip, an user cannot sense the excessive use of brushing pressure when the rubber bristles are deflected accordingly in the longitudinal direction of the bristle strip since the feel of the stiffness of the rubber bristle is still at the same order of magnitude as under a safe brushing pressure. Moreover, structurally, the strips are not attached to the periphery edge of a bristle platform, therefore, the effective cleaning area is reduced for a given size of a brush head.

U.S. Pat. No. 6,254,390 by Wagner uses a U-shaped oral burnisher head for simultaneously cleaning and/or burnishing multiple tooth surfaces. The burnisher head includes a pair of opposed side panels and an inner back panel, each of which has an array of thermoplastic elastomer projections. The arrays of projections of the two opposing panels are inwardly facing each other while having the array of projections of the inner back panel being situated in between. The objective of the device is simultaneously to engage the projections of the three panels with the labial, the lingual and the occlusal tooth surfaces for cleaning and burnishing at the same time. The elastomer projections have hemispherical tips extending from each panel base about one to two millimeters. A drawback of these projection tips is that, unlike bristles, they cannot penetrate under a gumline for effective cleaning. Besides, the projection pattern of the device is not shaped to conform to the profiles of the gumlines between teeth for focussed cleaning and massaging.

U.S. Pat. No. 3,553,759 by Kramer et al. describes a toothbrush for simultaneously cleaning teeth and massaging gumlines without damaging the gums. The toothbrush includes a central bristle section and a pair of longitudinal rows of outer rubber tips that are positioned on each side of the central section. The outer rubber tips are longer than the central bristles for protecting the gums from the brushing action of the central bristles. With the lower bristles in the center of the brush head, extra brushing force is needed for deflecting the outer rubber tips in order to reach and use the central bristles for cleaning teeth at a required brushing pressure. Once the central bristles are forced for brushing, there is no distint feedback to the user for warning the excessive use of brushing pressure on the central bristles. Consequently, gum damage still can occur with this type of toothbrush that uses longer outer rubber tips.

U.S. Pat. No. 3,258,805 by Rossnan relates to improvement in toothbrush by using bristles having thin rubber coating for producing erasing actions instead of a grinding action for cleaning teeth. By using rubber-encased bristles in the toothbrush, the gums are not scratched or torn while being massaged as possibly in the case of using conventional nylon or other stiffer bristles. Besides high manufacturing costs, functionally the tips of rubber coated bristles cannot effectively penetrate under gumlines for effective cleaning.

U.S. Pat. No. 5,628,082 by Moskovich describes the use of rows of resilient bars positioned at a distant from the edge of a brush head for massaging gums. Because the bars occupy the space that is normally used for implanting bristles for cleaning purpose, the cleaning capacity of the toothbrush is reduced. U.S. Pat. No. 4,277,862 by Weideman positions resilient massage members at the opposing longer sides of the brush head. Since the massage members are positioned in line with bristles at each of its ends and their heights are only slightly shorter than that of adjacent bristles for enabling polishing of the bristle tips during the manufacturing process, these massage members are not designed for preventing excessive brushing pressures and improper brushing angles. Also, the inline massage members reduce the number of bristles available for cleaning. Furthermore, the bases of the massage members are long and of continuous solid walls without having drainage openings for the passage of running water therethrough for cleaning, consequently, significant contamination can build up on the inner surface of the massage members.

On contamination, U.S. Pat. No. 5,346,324 by Kuo recognizes the positive and negative effects that air has on dentifrice dispensing toothbrushes. A toothbrush cover contains vent holes for air circulation to endure that the toothbrush bristles are properly dried between uses. Improper venting fosters contamination of the toothbrush with germs. The toothbrush cover also contains a plug for sealing the opening of a flow channel in the brush head. The sealing prevents air from contacting dentifrice in the flow channel, which prevents it from drying out and clogging the channel. The seal also prevents leakage of dentifrice material into the bristles during non-use periods. The presence of dentifrice material among wet bristles during inactive periods creates an unsanitary condition which could have an undesirable effect on the user's gums. While the patent discloses means for reducing toothbrush contamination, it makes no mention of the detrimental effects of improper brushing pressures and angles.

On the relationship between bristle pattern and brushing effectiveness, U.S. Pat. No. 4,667,360 by Marthaler, et al. discloses a preferable angular relationship between the bristle array surface and the handle for improving the force transfer from the handle to the working surface of the bristle array. U.S. Pat. No. 5,398,367 by Lu discloses preferred positions of soft and hard bristles in a brush head. For effective brushing, the soft bristles need to be longer while the hard bristles need to be shorter. With lower brushing force, only the soft bristles are in use giving minor cleaning and gum massaging. With strong brushing force, the hard bristles will be in use giving more effective cleaning, especially the space between the teeth. Its hard bristles are implanted away from the edge of the bristle pattern to be kept from being bent outward. Some bristles at the edge of the pattern are cut shorter to give the hard bristles a chance to get into space between the teeth. Because brushing entails continuous movement of a brush head, the spacing between, or the relative positions of individual bristle tufts have little effect on the effectiveness and comfort of brushing.

On securing a replaceable brush head to a toothbrush handle, it is well known that an unsecured connection can result in improper brushing angles and abrasion. Moreover, leakage of dentifrice material can occur in instances where a replaceable brush head is used with a self contained toothbrush that stores dentifrice material in brush handle.

The security of fastening a replaceable brush head is a subject of many patents in the prior art. U.S. Pat. No. 5,228,166 by Gomez uses a brush head which pivots longitudinally along the line of a handle. The head is fastened by a latch located in the handle of a toothbrush. The latch is held in place by a compression spring which permits the latch be easily disengaged to allow replacement of the brush head. Since the brush head is slidably and loosely engaged with a grooved rail and slot, the design, if used with a dentifrice dispensing toothbrush, cannot prevent the drying of toothpaste. A more secure brush head engagement is described in U.S. Pat. No. 4,155,663 by Cerquozzi which usesa threaded bore at the inlet opening end of a brush head. A problem is presented using this approach in aligning the orientation of a brush head with respect to a handle because of manufacturing tolerances of the threaded parts. In U.S. Pat. No. 5,224,234 by Arsenault, et.al., a brush head assembly is mated with the receptacle in a handle by utilizing five surfaces of sliding contact. Despite a perfect dimensional match in a manufacturing process, the dimensions of the receptacle may change after exposing to humidity and chemical reaction with the toothpaste after a period of usage. Consequently, a new brush may not be mountable on the receptacle of a used brush handle. Other methods of mounting a brush head are described in U.S. Pat. No. 5,875,510 by Lamond, et.al. The patent describes a neck of a brush head having a coupling anchor for engaging with a center-hollowed collar of a handle. The coupling anchor has a pair of outwardly flexible wings and the receiving collar has a locking feature with pins and a pair of outwardly flexible spring leaves. The release of the replaceable brush head is accomplished by pressing the pair of pins with finger action to disengage the spring leaves. The tightening of the brush head is enabled by compressing on a elastomeric pad and ribs which protrude from the surfaces of the plastic handle. The arrangement is not adaptable for use with a dentifrice dispensing toothbrush since the spring release mechanism would interfere with the flow channel of the toothbrush.

(3) Objects of the Invention

It is therefore an object of this invention to provide a toothbrush that has means for alerting a user when acceptable brushing pressures and angles are exceeded. It is another object of the invention to provide a toothbrush that is capable of providing selective and continuous massaging action on external gumlines as well as on targeted internal gumlines on the back of teeth without the risk of the bristles damaging gumlines. It is an additional object of this invention to provide a bristle pattern to prevent damage to bristles near the spout opening of a replaceable brush head by the sealing action of the plug. Still another object of this invention is to provide a contractible connector in the handle of a dentifrice dispensing toothbrush for reliably securing a replaceable brush head. These and other objects are accomplished in the manner described in the following descriptions.

SUMMARY OF THE INVENTION (1) Brief Description

The toothbrush of the present invention uses a rubber gum guard molded on the edge along the periphery edge of a brush head as a guide feature for providing feedback to an user regarding proper brushing pressures and angles during brushing. The rubber gum guard is formed as a wall having its height at a level lower than that of bristles for limiting the deflection and the pressure on the bristles. The distance of the rubber guard from opposing outer bristle tufts can limit the brushing angle against the gumline. The difference of heights between the rubber guard and the outer bristles is based on the stifffiess of bristles and desired maximum brushing pressure. The Durometer or hardness of the rubber wall material can be selected for providing distinct feel to serve as a feedback signal when the limit of brushing pressure or angle is reached.

Additionally, the rubber guard can be used for massaging gum tissues by stroking and sliding the outer surfaces of the rubber guard against the gum tissues. The rubber guard prevents bristles from contacting gum tissues, which can be sensitive to bristle contact for users with gum problems. Due to the resiliency of the rubber material, the top edges of outer surface of the guard wall can apply a pressure to massage gumlines without bristles touching or penetrating under the gumlines. These soft and large contact areas of the rubber guard provides comfort for massaging the outer gumlines. A rubber gum massage pad having contoured edges attached to the bottom surface of the distal end of the brush head can be used to reach and massage the gumlines on the back side of front teeth. With the gum massage pad on the bottom surface of the brush head, the massaging action is selective and totally separated from brushing which is mainly for cleaning and removing plaque from teeth. The massaging action is focussed on stimulating gumlines without the risk of damaging the gumlines.

The rubber guard and the rubber gum massage pad can be used on a toothbrush with a fixed brush head or with a replaceable brush head which can be replaced frequently for reducing the bacterial buildup. For adding convenience, a replaceable brush head may have a spout opening and be mounted on a permanent pump handle for dispensing dentifrice material from the pump handle to the top of bristles through the spout opening. For a replaceable brush head used in a dentifrice dispensing toothbrush, the present invention uses a plug having a sealing rod shielded by an annular wall for engaging the spout wall of dispensing opening in the brush head. The insertion of the sealing rod into the dispensing opening and the mating of the tight clearance between the sealing rod and the annular wall on the spout wall, as well as the sealing contact between the annular wall and the top of the spout wall can provide three levels of sealing the dispensing opening in the brush head for preventing toothpaste drying. For the convenience of sealing action, a bristle pattern is designed for initial lifting the plug and not blocking its path as the plug attached to a cover moves to pass bristle tufts most close to the dispensing opening to prevent stampeding of bristles on top of the dispensing opening. The plug is attached to a cover and can be self-located for sealing the dispensing opening.

The present invention also uses a resilient, molded-in rubber segment in the connector of a toothbrush handle to create a contractible outer diameter to accommodate the corresponding inside diameter of the neck of a brush head. In its free state, the outside diameter of the connector having the elastic segment in its annular wall is slightly larger than the corresponding inside diameter of the brush head neck. Upon insertion of the brush head on the connector, a slightly tapered lead-in surface of the brush head neck can force the annular connector wall to contract inward so as to allow total insertion of the brush head on the connector of the handle. Under the compression of the brush head neck, the elastic recovery nature of the compressed rubber segment creates a tightening and frictional force for locking the engagement between the brush head and the connector of the handle.

(2) Essential Components

The essential components of a preferred embodiment of a dentifrice dispensing toothbrush of the present invention includes; 1) a brush head having a bristle platform with an spout opening therethrough and to which a series of bristles are attached; 2) a slidable plug having a sealing rod surrounded by an annular wall for enclosing the spout opening of the brush head; 3) a brush cover having a guide feature for locating the slidable plug in a sealing position; 4) a handle having a contractible connector for mounting of the brush head and having a reservoir and a follower disc for storing dentifrice material, and the contractible connector has a resilient rubber segment on its annular wall; 5) a pump assembly which has a pump chamber and an elastic compressible button for supplying a pumping force and a base having a flap check valve; 6) a rubber guard attached to a brush head along its peripheral edge and said rubber guard has a form of a wall protruded above the bristle platform with the height of the wall at a level lower than that of bristles and having drainage holes and slots for the passage of running water therethrough for cleaning of the brush head; 7) a contoured rubber pad attached to the distal bottom surface of the brush head for effectively massaging gumlines at the back of teeth.

(3) Description of Essential Components and Functions

In operation, when the rubber button is depressed, a pumping force is applied which causes a quantity of dentifrice material to flow from a cavity in the rubber button and from the pump chamber through various conduits and to the brush head. During this time, back flow of dentifrice material from the pump chamber is prevented either by the one-way flap valve which is positioned at the base of the pump chamber. Upon release of the pump force, the rubber button returns to its original shape due to its resilient nature. This spring-back action creates a vacuum force which causes dentifrice material to flow into the cavity of the compressible rubber button. Concurrently, because of the required continuity of flow material, a quantity of dentifrice material moves from the reservoir in the handle into the pump chamber which in turn causes forward movement of a follower disc located at the bottom of the reservoir under the atmospheric pressure. The volume of dentifrice material being dispensed is equivalent to the volume displaced by the advancement of the follower disc. The forward movement of the follower disc keeps the remaining dentifrice material in a packed, void-free condition which ensures good pumping efficiency during subsequent use.

During brushing, bristles in contact with teeth and gums are deflected under a brushing pressure. The deflections make the bristles bend away from their original free straight states. There are spaces among tufts of bristles and between the outer bristle tufts and the inner wall of the rubber guard, which is positioned along the peripheral edge of the brush head. As bristles are over bent under pre-determined limit of brushing pressure, their effective heights become equal to the height of the rubber guard such that the rubber guard is exposed and in contact with the teeth and the gums. Upon sensing the touch of the rubber guard, the user can immediately reduce the brushing pressure to free the bristles from over bent positions such that the rubber guard is not in contact with the teeth and gums. During the course of brushing, numerous contacts with the rubber guard can occur as feedback for subsequent adjustments to reduce the brushing pressure. Similarly, the rubber guard does not contact the teeth and gums when brushing them at a proper angle. However, the contact also can occur when the brushing angle is too shallow beyond a limit at which bristles can penetrate too deep under the gum tissue to cause damage and bleedings. Again, the brushing angle can be adjusted instantly to avoid the contact of the rubber guard. These feedback and adjustments for brushing pressure and angle can happen continuously without interrupting the brushing movement. To facilitate cleaning the rubber guard has drainage holes and slots for the passage therethrough of running water.

Besides the function of preventing gum damages, the resiliency as well as the large area and edges of the rubber guard can be used for massaging gumlines. For massaging, the outer edge of the rubber guard can be used to stroke and slide against the gumlines and at this massaging position the rubber guard covers the gum tissues above the gumlines and separate the bristles from the gumlines. In this manner, the bristles can touch teeth by their sides but their tips cannot touch the gumlines to cause any discomforts. Nevertheless, the large curvature contour of the rubber guard cannot conform to the gumlines at the back of front teeth. To overcome this limitation, a resilient rubber gum massage pad with special contoured step and textured surfaces are attached to the bottom surface of the distal end of the brush head for massaging the small curvature area of the gum tissues and gumlines at back of upper and lower front teeth. In manufacturing, the rubber gum massage pad can be co-injection molded with the rubber guard. Because the rubber guard and the bottom gum massage pad do not occupy the bristle space of a conventional toothbrush their presence in the brush head do not reduce the effectiveness and efficiency of the regular brushing actions. Furthermore, the massaging actions of the rubber guard and the bottom gum massage pad on the gumlines are continuous without intermittent contacts of bristles with the gumlines. Therefore, these massaging actions provide comfortable sensation of gum stimulation.

The rubber guard and the bottom rubber gum massage pad features are preferably attached to a replaceable brush head to be used in a dentifrice dispensing toothbrush, which dispenses dentifrice material form its cartridge handle to the spout opening of the replaceable brush head. For preventing drying of dentifrice material at the spout opening, a plug having a sealing rod surrounded by an annular groove and wall is used for inserting the sealing rod into the spout opening and for mating the annular groove with the annular wall of the spout opening for air-tight engagement. In addition, the plug is slidably attached to a cover having guide features for facilitating self-locating of the plug for sealing the spout opening and for locking the plug in a position which enables the bottom of the annular groove to be in tight contact with the top of the annular wall when the plug is fully latched on the cover which is being mounted on the toothbrush. All the above reinforcing sealing features of the plug provide multiple barriers to air contact with the dentifrice material inside the brush head.

In conjunction with the self-locating feature of the cover for sealing plug, a bristle pattern is designed to avoid stampede of bristles when inserting the sealing rod into the spout opening. Along the travel path of the sealing rod in the direction of mounting a cover on a handle, a series of bristle tufts are positioned on the central plane in the way of plug travel for lifting the sealing rod away from the platform of the brush head. A plurality of bristles near the end of sealing-rod travel toward the spout opening are positioned apart from the central plane to provide non-obstructing space for the travel of the sealing rod such that no bristles can be stampeded on top of spout opening during the insertion of the sealing rod into the spout opening.

Furthermore, a contractible feature is built in the connector of a dentifrice dispensing toothbrush for mounting of a replaceable brush head. The contractible feature utilizes a molded-in rubber segment in the annual wall of the connector which has a flow channel connected to the reservoir inside the handle. The rubber segment is co-injection molded across the thickness of the annular wall of the connector such that the compression of the rubber segment in the angular direction can reduce the effective outside diameter of the annular wall. In the free state, the outside diameter of the composite annular wall of the contractible connector is slightly larger than that of the corresponding inside diameter of a brush head neck, which has tapered inner wall section at the base of the opening and nontapered tapered inner wall section away from the base. At the beginning of mounting the brush head, the inside diameter of slightly tapered inner wall of the neck portion is slightly larger than the outside diameter of non-tapered outer wall of the contractible connector. Further insertion can cause the inner wall of the neck portion to compress on the annular wall of the contractible connector to contract inward which is possible due to the resiliency of the rubber segment. When the brushead is fully mounted the tapered and non-tapered portions of the neck can match with the corresponding tapered and non-tapered portions of the contractible connector, respectively. Under compression, the elastic recovery nature of the rubber segment increases the friction force between the mating parts and the tightening of their engagement. Moreover, the security of the mounting can be strengthened by lengthening the contact walls of the two mating parts. Also, in the present invention, the use of rubber segment in the contractible connector enables a molded-in rubber button, whose injection flow path can be connected to the rubber segment of the contractible connector which serves as a gating point for the co-injection flow.

BRIEF DESCRIPTION OF THE DRAWINGS

FIG. 1a is a perspective view of the toothbrush of this invention.

FIG. 1b is a perspective view showing the bottom of the head of the toothbrush of FIG. 1a.

FIG. 3b is a cross section view of a dentifrice dispensing toothbrush with the brush head detached from the handle.

FIG. 3c is a cross section view of a dentifrice dispensing toothbrush shown in FIG. 3b with the brush head attached to the handle.

FIG. 4a is a perspective view of a plug showing a cross section view of a sealing tip and rod.

FIG. 4b is a plan view of the underside of the plug of FIG. 4a.

FIG. 4c is a perspective view showing the underside of the plug of FIG. 4a.

FIG. 4d is a cross section view of a toothbrush head showing a plug inserted into a spout opening in the bristle platform of a brush head.

FIG. 5a is a cross section view of a dentifrice dispensing toothbrush with a cover and a plug in an unseated position.

FIG. 5b is a cross section view of the toothbrush shown in FIG. 5a with the plug in its seated position.

FIG. 6b is a cross section view of a brush head aligned for attachment to the pump housing and contractible connector shown in FIG. 6a.

FIG. 6d is a perspective view of the pump housing and contractible connector shown in FIG. 6a.

DETAILED DESCRIPTIONS OF THE PREFERRED EMBODIMENT

Figure 1C:
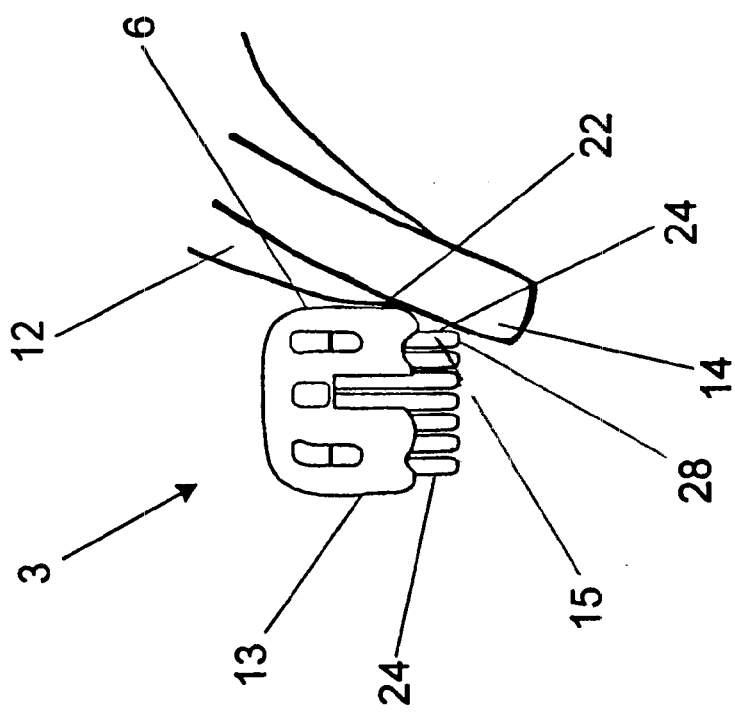
FIG. 1c is a side elevation of a brush head positioned against a tooth and its gum tissue.

FIGS. 1a, 1b, 1c, 1d, and 1e shows a toothbrush 1 with a brush head 3 and handle 21. Brush head 3 has bristle platform 7 having a peripheral edge 13' that extends from the top surface 7' to the bottom surface 25 and rubber guard 5 attached to the peripheral edge of the bristle platform 7. (The terms, "rubber gum guard", "resilient gum guard", "resilient guard wall", "resilient guard", "rubber guard" and "rubber guard wall" are used interchangeably.) A plurality of outer bristles 15 and inner bristles 15' are attached to the bristle platform. The rubber guard 5 is divided into wall segments 13 by slot openings 11, which provide for the passage of cleaning water and which add to the flexibility of the wall segments. A plurality of saddle valleys 17 and peaks 19 are positioned at the top of rubber guard wall 5. The length, L, of wall segment 13 is longer than the distance, D, between the centers of two adjacent tufts of outer bristles 15 for ensuring rigidity in the length direction of the wall segment. Drainage hole 9 in wall segment 13 is for enabling flexibility in the thickness direction of the wall segment. Wall segments 13 serve as a deterrent to improper brushing by providing a barrier between the bristles 15 and the gums during brushing. The wall segments are deflected outward when a high brushing pressure is applied and are deflected inward when a shallower brushing angle is needed for special cleaning purposes. Wall segments and their flexibility permit the use of brushing pressures and angles which are beyond manufacturer recommended normal ranges yet serve to warn the user when improper brushing pressures and angles are utilized. However, the stiffness of a wall segment in its length direction is required for effective massaging when the brush head is used upside down, as shown in FIG. 1c, in the longitudinal direction of the brush head.

Figure 1E:
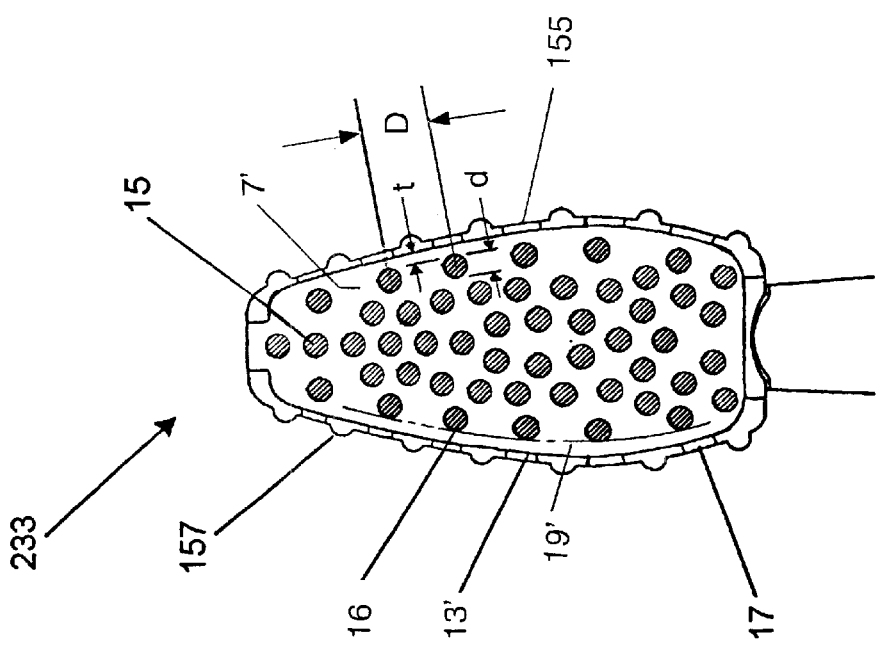
FIG. 1e is a plan view of the brush head shown in FIG. 1d.

Slot openings 11, saddle valleys 17 and peaks 19 of wall segments 13 are positioned to accommodate the deflections of outer bristles 15. Excessive brushing pressure causes outer bristles 15 being pushed into the slot openings 11 or in saddle valleys 17 which result in contact between wall segments and the gums. Such contact indicates that the brushing pressure should be adjusted. The height of resilient guard wall 5 is less than the height of outer bristles opposing to the rubber guard. The optimum height of the rubber guard depends on the stiffness of the outer bristles and generally ranges from 50% to 80% of the height of the opposing outer bristles. Referring to FIG. 1e, the border distance, t, between the inner surface of the resilient guard wall 155 (or a wall segment) and the outer perimeter surface 19', tangent to tuft holes 16 of outer bristles 15, is a critical parameter in determining the limit of proper brushing angle.

The border distance or the width of the gap has an effect on the proper functioning of the rubber guard wall. For a given height difference between outer bristles 15 and the guard wall segments 13, the optimum width of the gap between them is determined by the minimum brushing angle that may be used without damaging the gum tissues. The width of the gap is preferably at least 20%, and up to 50% of the height of outer bristles opposing to the guard wall segments.

The toothbrush shown in FIG. 1a is fabricated by using co-injection molding and bristle implanting technologies. Outer and inner bristles are preferably made from a nylon material. The bristle platform 7, and the handle 21 are thermoplastic materials while resilient guard 5 is either a rubber or a thermoplastic elastomer material. To reinforce the bonding of two materials, notches are created along the edge of the platform as anchoring sites for mechanical locking of the rubber material 23. FIG. 1b shows a configuration that extensions 23 of resilient guard 5 are joined to bottom side 25 of bristle platform 7 in the fabrication process to cover notch areas (not shown) for mechanical locking of different molding materials.

The objective of the guard wall for making the user aware of reaching the limits of brushing pressure and angle is accomplished by using various shapes, forms and material for the resilient guard wall. The top of resilient guard wall 5 may be a plurality of peaks and valleys, 19 and 17, or a plurality of studs or it may be smooth or any other configuration that provides a different and distinct sense of feel when in contact with the user's gums. In this regard, the resilient guard wall is fabricated from any suitable flexible, thermoplastic or foam material.

Figure 1D:
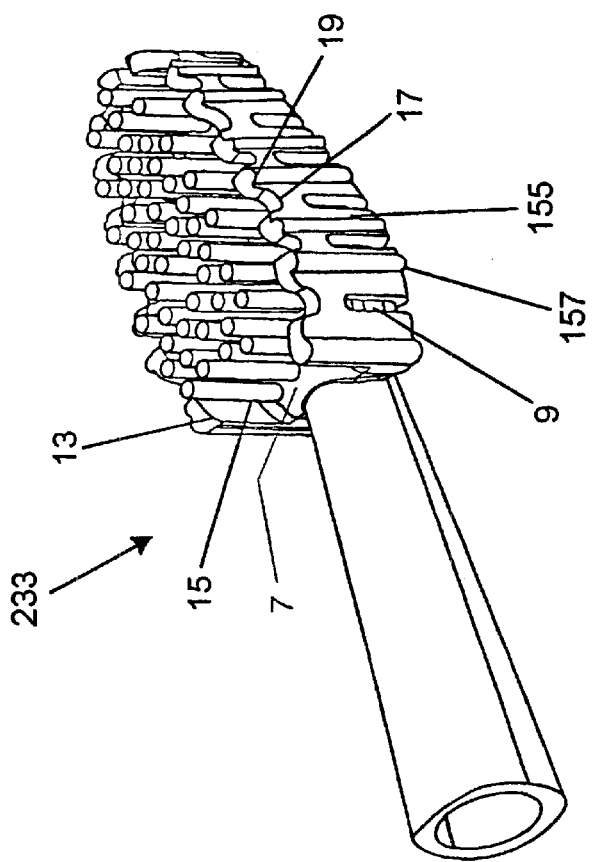
FIG. 1d is a perspective view of a brush head with a ribbed guard wall connected to its peripheral edge.
Figure 2A:
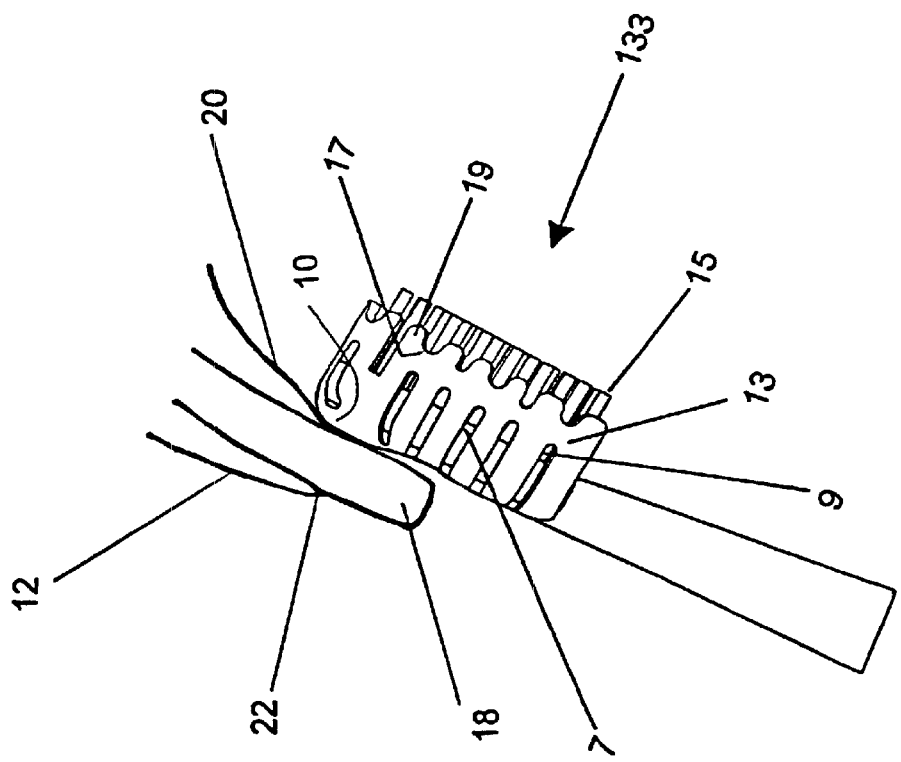
FIG. 2a is a front elevation of a brush head with its bottom surface positioned against gum tissue behind a front tooth.
Figure 2C:
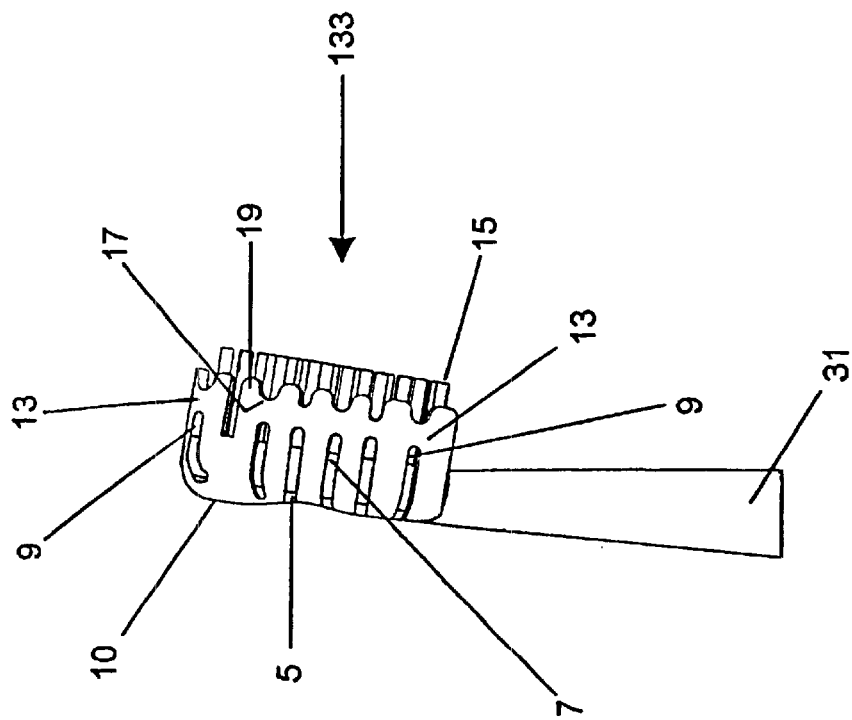
FIG. 2c is a front elevation view of a brush head showing a rubber gum massage pad attached to the bottom of a rubber guard.
Figure 2B:
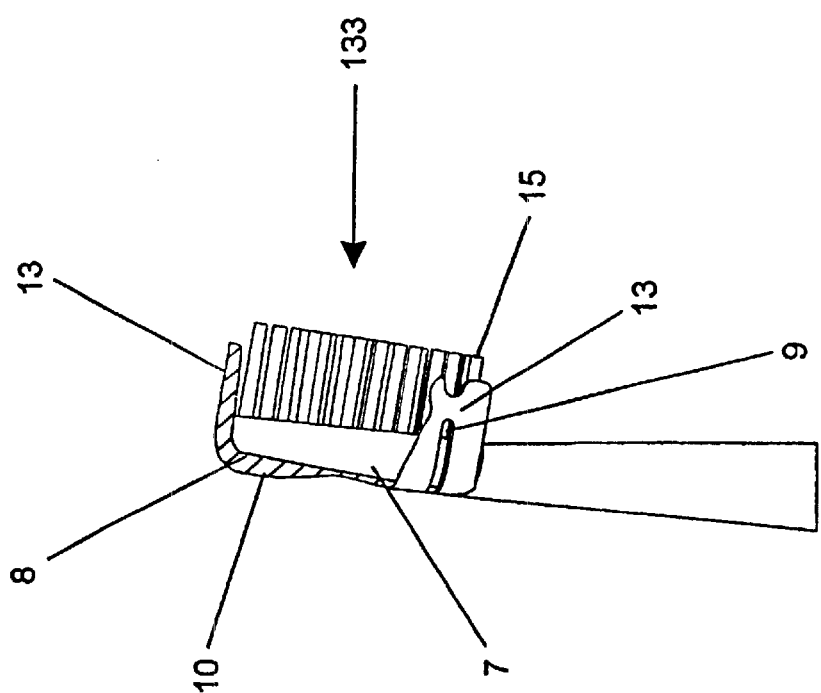
FIG. 2b is a partial cross-section view of the brush head shown in FIG. 2c.

As shown in FIG. 1c, rubber guard 5 and wall segments 13 are used to massage gum tissue 12 and gumline 22. During brushing, outer surfaces 6 of guard wall segment 13 massages gum issue 12 and gumline 22 while bristle tips 28 contact the surface of tooth 14. In a massaging position the rubber guard 5 and wall segments 13 cover the gum tissues 12 above the gumline 22 and separate outer bristles 15 from the gum tissues 12 and gumline 22. Sides 24 of outer bristles 15 touch teeth 14 but their tips 28 are positioned beyond the gumline 22 and are not able to touch the gumline 22 to cause any discomfort. Alternatively, the segmented walls can be joined to become a continuous wall to increase wall rigidity during massaging as shown in FIG. 1d. FIG. 1d also shows a plurality of ribs 157 on the outer surface of the rubber Luard 155 of brush head 233 for massaging low areas between teeth. FIG. 1e is a top view of brush head 233 showing the outer profile of continuous rubber guard 155 with ribs 157. As shown in FIG. 2a, a rubber massage pad attached to the distal bottom surface area 8 of the brush head 133 is used to massage gum tissues 20 behind front teeth 18. FIGS. 2b and 2c show resilient rubber gum massage pad 10 attached to distal bottom 8 of brush head 133. The rubber gum massage pad 10 is co-injection molded with rubber guard wall 5.

Figure 2F:
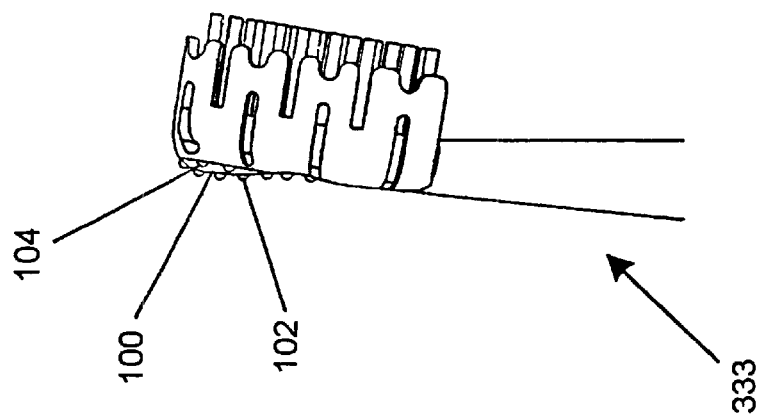
FIG. 2f is a front elevation of a brush head showing cleats on a rubber gum massage pad surface as positioned on the bottom of the brush head.
Figure 2E:
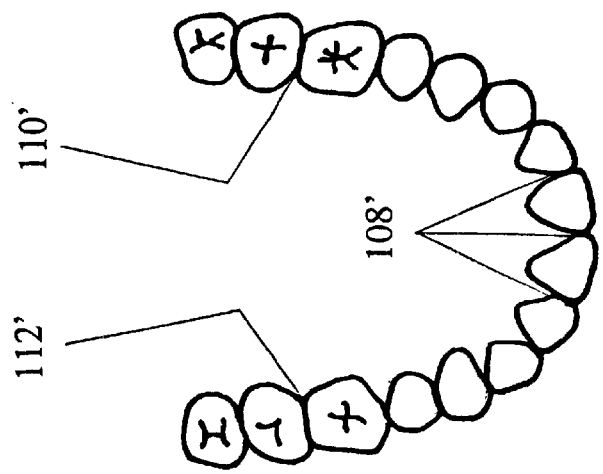
FIG. 2e is a pattern outline of an upper or lower set of teeth.
Figure 2D:
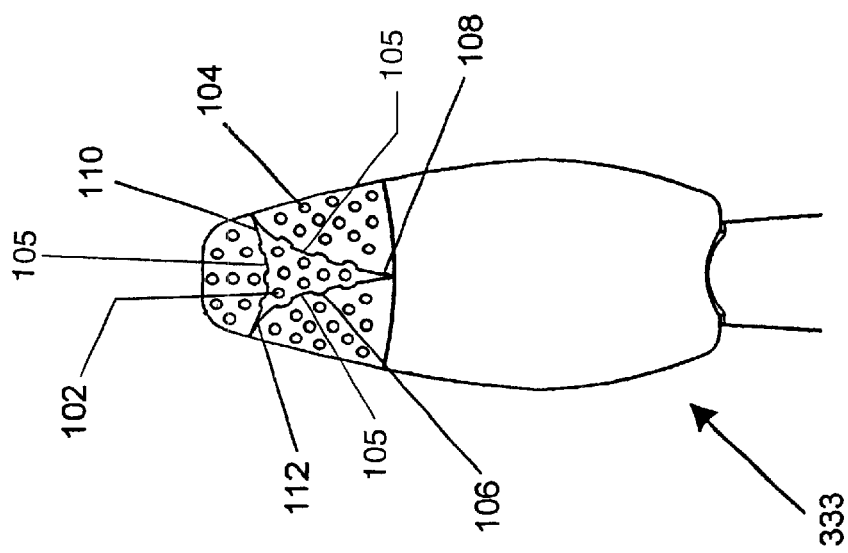
FIG. 2d is an outline of a plan view of the bottom of a brush head showing a triangular elevated surface and cleats on the surface of a rubber gum massage pad.

For targeted massaging the gumlines and removing plague from the back of front teeth, a triangular elevated surface 100 is positioned on the surface of rubber gum massage pad of a brush head 333 as shown in FIGS. 2d and 2f. The concave profile 105 of each edge of the apexes 108, 110 and 112 of the triangular elevated surface 100 conforms to the shape of gumlines at the back of front teeth as shown in FIG. 2e. A plurality of cleats 102 are placed on the triangular, elevated surface 100, and a plurality of cleats 104 are placed on the lower surface of rubber gum massage pad 10, to enhance cleaning and massaging. At a massaging position for massaging the back of front teeth, apex 108 is aligned with the gumline 108' between two front teeth. While in this position during massaging, the brush head is pressed against the back of the teeth and pulled away from the gum tissue. Cleats 106 along the edges along triangular shaped gumlines. Similarly, apex 110 and apex 112 are used for massaging gumlines at the back of other teeth where the brush head is naturally at an incident angle with the jaw line. The orientation of apexes 110 and 112 are designed to fit best with the shape and directions of gumlines 110 and 112 at the back of side teeth other than the front teeth and those nearby. Cleats 104 provide additional cleaning by their massaging action. Because wall segments 13 and rubber gum massage pad 10 do not occupy bristle implanting space, the brushing efficiency is not reduced during regular brushing action.

Figure 3A:
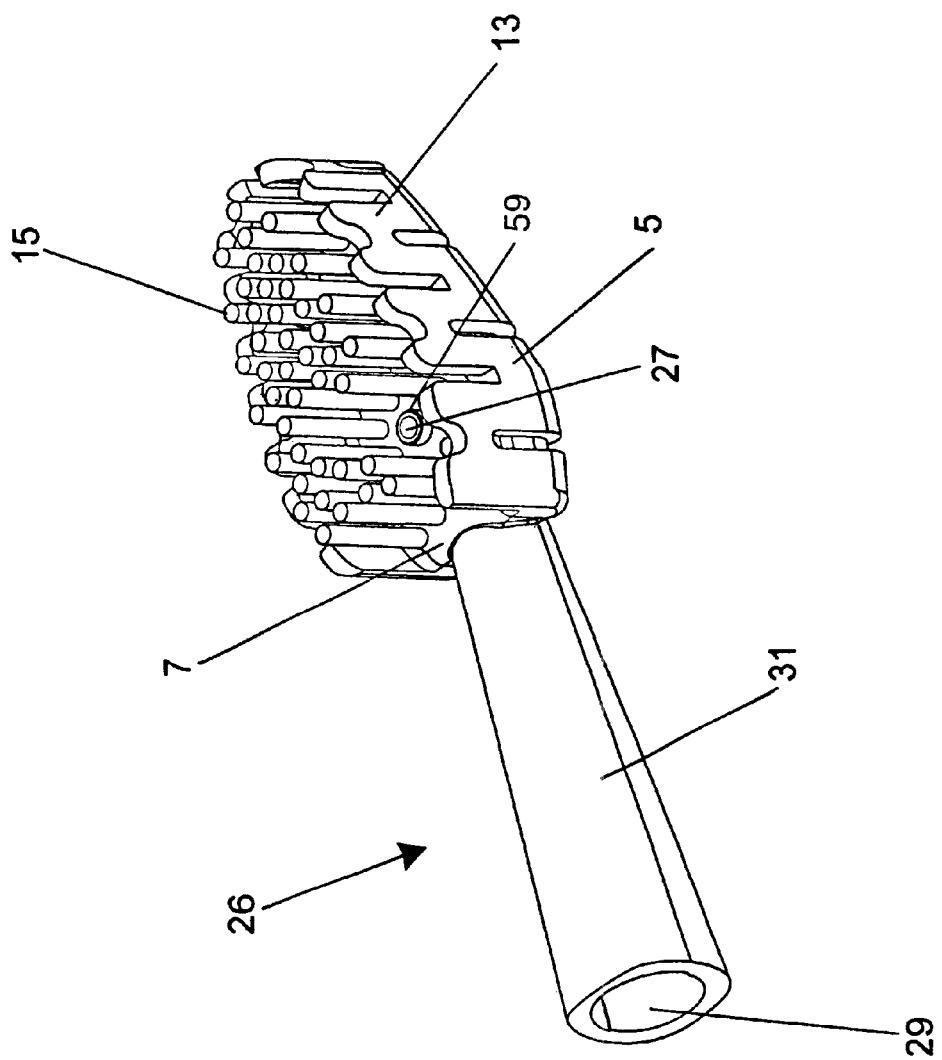
FIG. 3a is a perspective view of a replaceable brush head for a dentifrice dispensing toothbrush.

The rubber guard is used on the bush head of a conventional toothbrush, or on a replaceable brush head that of an electrical toothbrush or of a dentifrice dispensing toothbrush. In FIG. 3a, rubber guard wall segments 13 are attached to a replaceable brush head 26 of a dentifrice dispensing toothbrush. The replaceable brush head has a bristle platform 7, outer bristles 15, inner bristles 15' and a spout opening 27 connected to a flow conduit 29 which is inside neck 31. Neck 31 is connected to a brush handle that has a reservoir for dentifrice material. Rubber guard 5 is attached at a distance, t (shown in FIG. 1e), to the periphery edge of bristle platform 7 forming a gap between the rubber guard and the outer bristles.

FIGS. 3b and 3c show replaceable brush head 26 with dentifrice dispensing cartridge handle 38 which stores dentifrice material in reservoir 35. Neck 31 of a replaceable brush head 26 attaches to contractible connector 33. A pump assembly 38 includes pump housing 34, pump chamber 37, compressible rubber button 39 for applying a pumping force and a flop check valve 42 at the base of chamber 37. Contractible connector 33 is attached to and a part of pump housing 34. The base of pump housing 34 is secured to reservoir 35 in handle 38 by threads 44. When compressible rubber button 39 is depressed, dentifrice material is pumped from reservoir 35 through flow channel 45 in the contractible connector, through conduit 29 in the brush head and through spout opening 27 (FIG. 3a) to the surface of the bristles.

A sealing mechanism for the spout opening in a brush head is shown in FIGS. 4a, b, c, and d. Plug 47 has a slidable saddle flange 49 and a sealing rod 51 positioned on its underside. At the end of the sealing rod, is a sealing tip 53 that is surrounded by annular groove 55 and annular wall 57. The exterior surface of annular wall 57 is oval shaped and is positioned so that its longitudinal axis terminates at opposite ends 54 and is aligned in the same direction as open ends 61 of saddle flange 49. A pair of guide ribs 58 are positioned on the underside of the slidable saddle flange 49.

FIG. 4d shows plug 47 in full sealing engagement with the spout opening wherein sealing tip 53 is inserted into the spout opening and annular groove 55 is mated with the top of the wall of the spout opening 27. To ensure a tight fit, sealing rod 51 is made of a softer sealing material such as thermoplastic elastomer or rubber and the width of the annular groove 55 is slightly less than the thickness of the spout wall 59. The spout wall 59 is preferably made from a harder thermoplastic material and has rounded lead in corner for the ease of mating of the two parts. A tight seal is achieved by latching saddle flange 49 to guide slots (not shown) on a cover for the toothbrush. This maintains the bottom of annular groove 55 in close contact with the top of the annular spout wall 59 of the spout opening 27.

As shown in FIG. 5a, plug 47 is attached to cover 46 for replaceable brush head 26. Sealing rod 51 is positioned in an aperture in the cover which is aligned with spout opening 27 when the cover is fully mounted on the shoulder 40 of pump housing 34. Guide slots (not shown) are positioned on the outside wall of cover 46 to correspond to guide ribs 58 on the inner surface of plug flange 49 (FIG. 4a). The guide slots and ribs ensure that sealing tip 53 is aligned for full insertion into spout opening 27 and proper mating of annular groove 55 of sealing tip 53 with annular wall 59 of spout opening 27. While the various sealing features preclude air contact with the dentifrice material to prevent drying and caking of dentifrice material beneath the sealing tip, holes 62 through the top of cover 46 and holes 63 through the side walls of the cover allow air to circulate to dry the bristles.

Figure 6C:
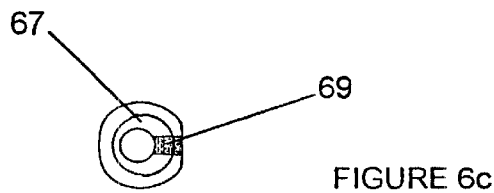
FIG. 6c is a plan view of the connector showing rubber segment across thickness of a contractible connector wall.
Figure 6B:
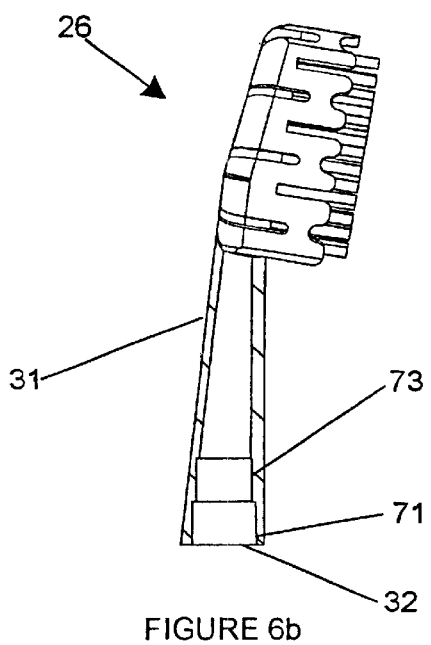
Figure 6D:
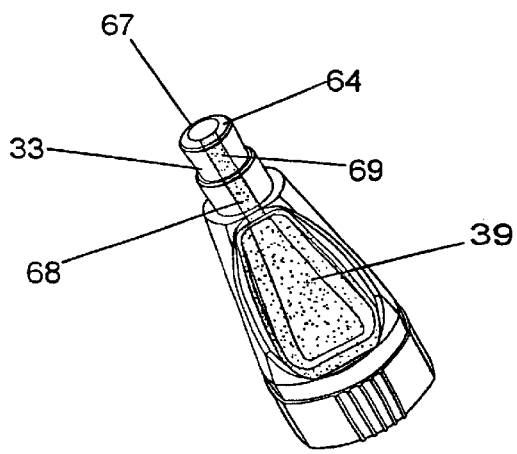
Figure 6A:
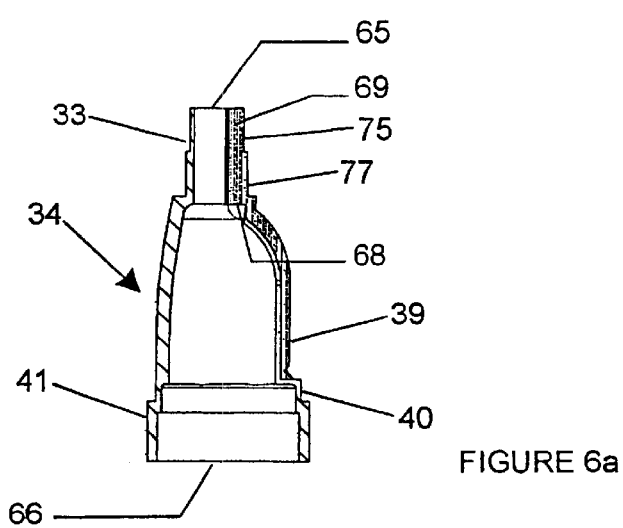
FIG. 6a is a cross section view of a pump housing and contractible connector for a dentifrice dispensing toothbrush.

FIG. 6a shows a orthogonal side view of a contractible connector 33 and a pump housing having outlet opening 65 and inlet opening 66. Inlet opening 66 is within base 41 which has a one-way flap valve 42 with thread 44 for mounting a brush handle which stores dentifrice material as shown in FIG. 3b. The outlet opening is in the contractable connector which is for connection to neck 31 of a brush head 26. As shown in FIG. 6d, contractible connector 33 of the pump housing 34 has an annular wall 67 that has a rubber segment 69 across the thickness of the annular wall for enabling the contraction of the connector wall under compression pressure. Rubber segment 69 extends from the top opening through base 68 and terminates at compressible rubber button 39. The position of rubber segment 69 in the contractible connector is shown in FIG. 6c. Base 68 of contractible connector 33 has a tapered outer surface 77 while annular wall 67 has a non-tapered outer surface 75. Neck 31 has a tapered inner wall section 71 which corresponds in shape to and is mateable with tapered outer surface 77. Neck 31 also includes a non-tapered inner wall section 73 adjacent to tapered inner wall section 71. The shape of non-tapered inner wall section 73 corresponds to the shape of, and is mateable with non-tapered surface 75. In the free state, the dimension (or equivalent diameter) across the outside of annular wall 67 is slightly larger than the maximum inside dimension across inner wall section 73. Also, in the free state the maximum dimension (or equivalent diameter) across the outside of base 68 is slightly larger than the maximum inside dimension across inner wall 71. At the time of the initial insertion of contractible connector 33 into neck 31 as a brush head is being attached to its handle, the inside equivalent diameter of slightly tapered inner section wall 71 of the neck is slightly larger than the equivalent outside diameter of base 68 of the contractible connector. Insertion of contractible connector 33 into neck 31 causes the inner walls 71 and 73 to compress on the non-tapered wall surface 75 and tapered wall surface 77 of the contractible connector which causes their inward contraction. When a brush head is fully mounted, tapered inner wall 71 and non-tapered inner wall section 73 of the neck match with the corresponding tapered outer surface 77 and non-tapered outer surface 75 of the contractible connector, respectively. Under compression, the elastic recovery nature of the rubber segment 69 increases the friction force between the mating parts and tightens their engagement. The non-tapered sections of the two parts maintain an adequate frictional force against any pulling force that occurs during the brushing motion. This feature helps to prevent accidental separation of the brush head from the contractible connector during use. Lengthening the non-tapered walls 73 and 75 of the two mating parts strengthens the connection of the parts which increases the friction force. The brush head is detachable by the application of a pulling force that is sufficient to overcome the friction force of the contractible connector wall under compression pressure.

In the embodiment shown in FIG. 6d, rubber segment 69 is connected to elastic compressible rubber button 39 used for pumping dentifrice material from the pump chamber to brush head 26. The connection of rubber button 39 and rubber segment 69 increases the length of the resiliency of the combined unitary structure that adds contractibility to the connector wall. It also enables the top annular wall 67 of the contractible connector 33 for gating of co-injection molding flow to achieve a smooth surface appearance for the rubber button 39 without creating a gating mark. The elimination of such marks is desirable in the manufacture of consumer products. Alternatively, rubber button 39 and annual wall 67 of the contractible connector can be made of one single material such as a flexible thermoplastic elastomer that has desirable sealing and contractility properties under a compression force.

Figure 7A:
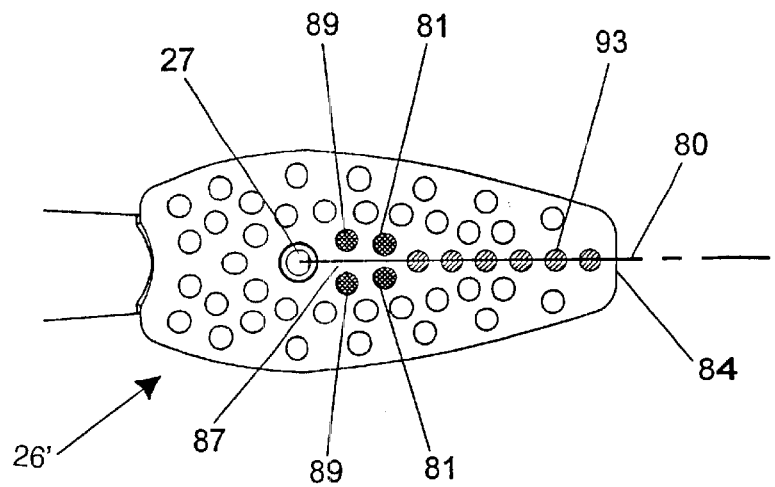
FIG. 7a is a plan view of a bristle pattern for a dentifrice dispensing toothbrush.

FIG. 7a shows a bristle pattern that is another aspect of the present invention. The pattern is used in conjunction with plug 47 for sealing the spout opening 27 of a brush head 26'. The bristle pattern prevents stampeding of bristles when the sealing tip is inserted into the spout opening 27. Attached to the bristle platform 84 of brush head 26' are a set of central bristles 93 positioned inline with the central plane 80 of bristle platform 84, whose peripheral edge is symmetric to the central plane, and a set of offset bristles 89 and 81 positioned symmetrically apart with respect to the central plane and located between spout opening 27 and central bristles 93. The offset bristles are for providing open space 87 near the spout opening.

Figure 7B:
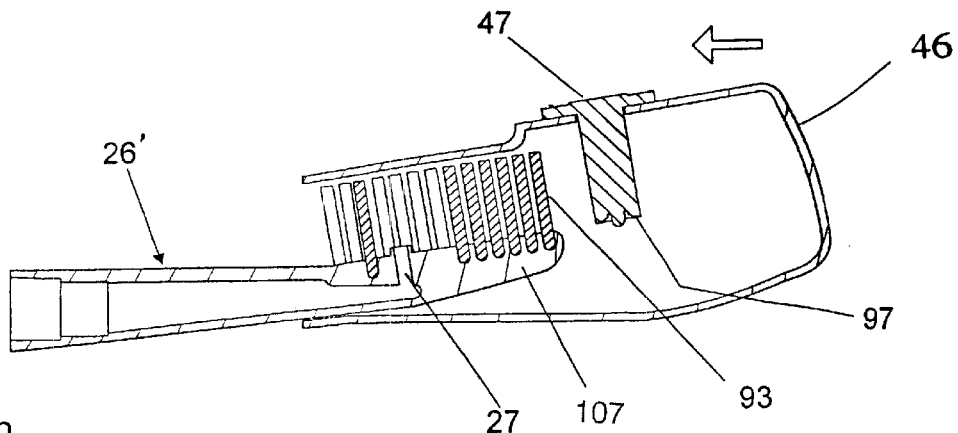
FIGS. 7b, 7c, 7d, 7e and 7f are cross section views of a cover and brush head of a dentifrice dispensing toothbrush showing the sequential positions of a plug as the cover is placed on the brush head.
Figure 7C:
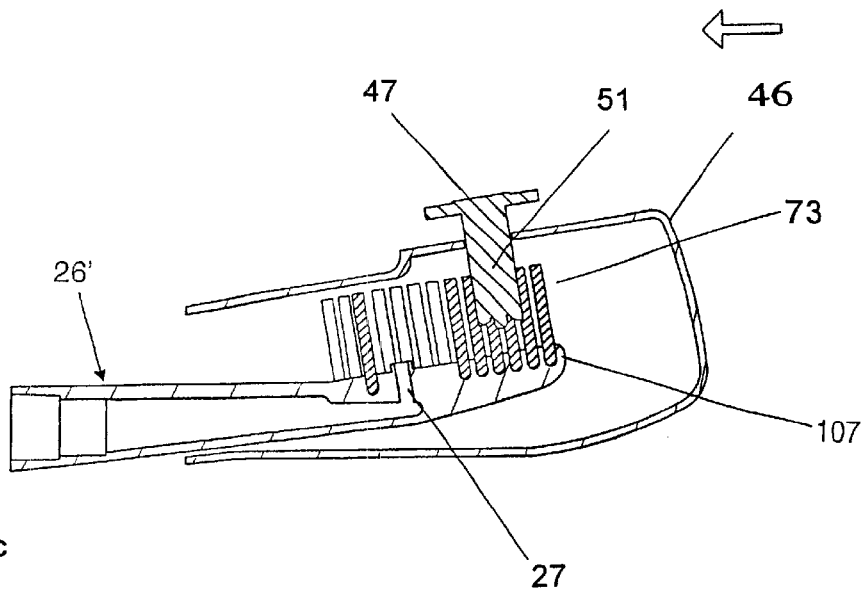
Figure 7D:
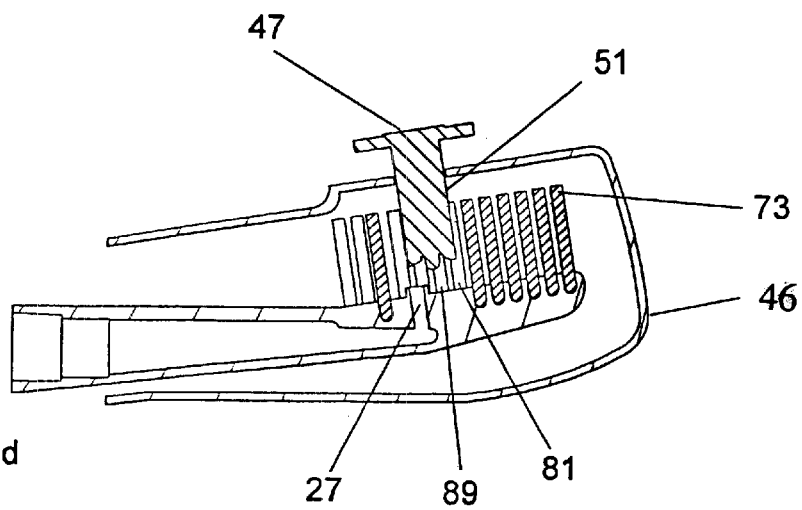
Figure 7E:
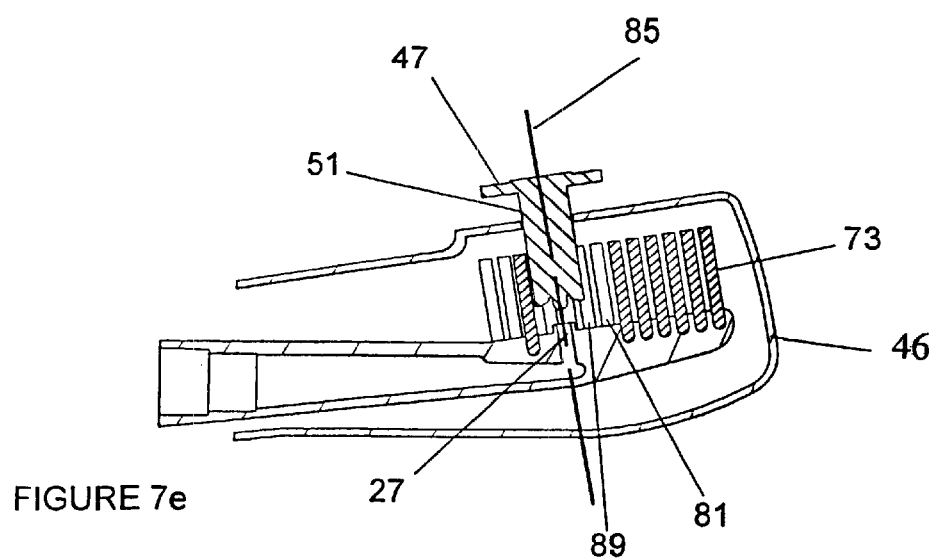
Figure 7F:
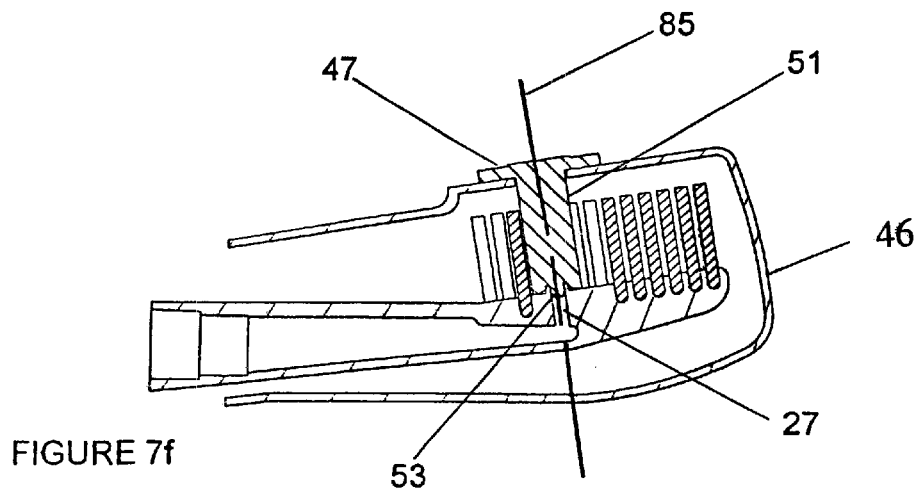

FIGS. 7b, c, d, e, and f sequentially shows the movement and positioning of plug 47 as cover 46 is placed on a dentifrice dispensing toothbrush. As shown in FIG. 7b, plug 47 is at its lowest position prior to its contact with bristles 93. FIG. 7c shows the plug being lifted away from the bristle platform 107 as plug 47 and sealing rod 51 are pushed upward by the bristles 93 which are in the travel path of the plug as it moves toward spout opening 27 inline with the central plane 80. Lifting of plug 47 is necessary to elevate it over spout opening 27 that extends above the surface of bristle platform 107. FIG. 7d shows the position of sealing rod 51 above open space 87 (shown in FIG. 7a) adjacent to spout opening. FIG. 7e shows the final alignment of sealing rod 51 above spout opening 27 with cover 46 in its final mounted position. Any stray bristles that may remain in the travel path, which is inline with the central plane, or open space 87 are pushed aside by the wedge-shaped front end 83 of sealing rod 51 (FIG. 4b). From its final aligned position 85, plug 47 is manually pushed downward as it is guided in place by ribs 58 (FIG. 4a) which are mated with corresponding grooves (not shown) on cover 46. As plug 47 is pushed downward, sealing tip 53 is inserted into spout opening 27. The tapered edges 97 of sealing tip 53 push aside any bristles that may be present in the sealing tip area. FIG. 7f shows the plug, rod tip and spout opening in the final sealed position.

The invention has been described in detail with reference to a preferred embodiment thereof. However, it is understood that variations and modifications can be effected within the spirit and scope of the invention.

I claim:

1. A toothbrush comprising a brush head having:
   a. a bristle platform having a top surface, a bottom surface and a peripheral edge that extends from the top surface to the bottom surface;
   b. a plurality of outer and inner bristles attached to the top surface of said platform, said outer and inner bristles defining at their free ends a brush surface; and
   c. a resilient guard wall having a base attached to the peripheral edge of said bristle platform, and an unattached top which terminates below said brush surface, and said resilient guard wall having a plurality of wall segments separated by slot openings and being positioned with a gap opposing to the outer perimeter surface of said outer bristles, and each wall segment having a drainage hole which is extending from the top surface of the bristle platform and the length of each wall segment being longer than the distance between the centers of two adjacent tuft holes of the outer bristles opposing to the wall segment.

2. A dentifrice dispensing toothbrush comprising:
   a. a replaceable brush head having:
      i. a bristle platform having a top surface, a bottom surface, and a peripheral edge that extends from the top surface to the bottom surface;
      ii. a plurality of bristles attached to the top surface of said bristle platform;
      iii. a spout opening which extends through the bristle platform;
      iv. a spout wall which extends from the top surface of the bristle platform and is in communication with the spout opening in the bristle platform; and
      v. a neck having a base with an inlet opening which is in communication with the spout opening in the bristle platform.
   b. a handle having:
      i. a reservoir for storing dentifrice material;
      ii. pumping means for pumping dentifrice material from the reservoir to the brush head; and
      iii. a contractible connector for mounting said brush head, said contractible connector being comprised of an annular tubular wall having a rubber segment across the thickness of the annular tubular wall, and an internal channel which is in communication with the reservoir and the spout opening.

3. The dentifrice dispensing toothbrush of claim 2 includes a gum massage pad attached to the bottom surface of said bristle platform and said gum massage pad has triangular shaped edges forming three apexes for massaging gum lines between teeth.

4. The dentifrice dispensing toothbrush of claim 2 wherein said pumping means includes pump chamber having an inlet, an outlet and an elastic rubber button for supplying a pumping force.

5. The dentifrice dispensing toothbrush of claim 4 wherein the rubber segment of the annual tubular wall of the contractible connector and the compressible rubber button are joined together to form a unitary rubber structure.

6. A dentifrice dispensing toothbrush of claim 2 wherein said replaceable brush head has outer and inner bristles defining at their free ends a brush surface and a resilient guard wall having a base attached to the peripheral edge of said bristle platform, and an unattached top which terminates below said brush surface, and said resilient guard wall having a plurality of wall segments separated by slot openings and being positioned with a gap opposing to the outer perimeter of said outer bristles, and the length of each wall segment being longer than the distance between the centers of two adjacent tuft holes of the outer bristles opposing to the wall segment.

7. A dentifrice dispensing toothbrush comprising:
   a. a brush head having:
      i. a bristle platform having a top surface, a bottom surface and a peripheral edge that extends from the top surface to the bottom surface, said peripheral edge being symmetric with respect to the central plane of the bristle platform;
      ii. a spout opening positioned inline with the central plane of the bristle platform and said spout opening extends through the bristle platform;
      iii. a spout wall which extends from the top surface of the bristle platform and is in communication with the spout opening in the bristle platform; and
      iv. a plurality of bristles which are attached to said bristle platform, said bristles include a set of central bristles positioned inline with the central plane of the bristle platform and a set of offset bristles positioned symmetrically apart with respect to the central plane and located between the spout opening and said set of central bristles;
   b. a cover for protecting the brush head;
   c. a plug being slidably attached to the cover for sealing said spout opening, and said plug comprising:
      i. a rod having a top end and a bottom end;
      ii. a sealing ring comprised of an annular groove positioned in the bottom end of the rod in a manner such that the annular groove is mateable with the spout wall for sealing the spout opening;
   d. a handle having:
      i. a reservoir for storing dentifrice material;
      ii. a pumping means for pumping dentifrice material from the reservoir to the spout opening;
      iii. a connector for mounting said brush head, said connector having an internal channel which is in communication with the reservoir and the spout opening of the brush head.

8. A dentifrice dispensing toothbrush comprising:
   a. a brush head having:
      i. a bristle platform having a top surface, a bottom surface and a peripheral edge that extends from the top surface to the bottom surface, said peripheral edge being symmetric with respect to the central plane of the bristle platform;
      ii. a spout opening positioned inline with the central plane of the bristle platform and said spout opening extends through the bristle platform;
      iii. a spout wall which extends from the top surface of the bristle platform and is in communication with the spout opening in the bristle platform; and
      iv. a plurality of bristles which are attached to said bristle platform, said bristles include a set of central bristles positioned inline with the central plane of the bristle platform and a set of offset bristles positioned symmetrically apart with respect to the central plane and located between the spout opening and said set of central bristles;
b. a cover for protecting the brush head;
c. a plug being slidably attached to the cover for sealing said spout opening, and said plug comprising:
  i. a rod having a top end and a bottom end;
  ii. a sealing ring comprised of an annular groove positioned in the bottom end of the rod in a manner such that the annular groove is mateable with the spout wall for sealing the spout opening.
d. a handle having:
  i. a reservoir for storing dentifrice material;
  ii. a pumping means for pumping dentifrice material from the reservoir to the spout opening;
  iii. a connector for mounting said brush head, said connector having an internal channel which is in communication with the reservoir and the spout opening of the brush head.

\* \* \* \* \*